United States Patent
Tijm et al.

(10) Patent No.: US 9,290,425 B2
(45) Date of Patent: Mar. 22, 2016

(54) PRODUCTION OF MIXED ALCOHOLS FROM SYNTHESIS GAS

(71) Applicants: Peter J. Tijm, Glenwood Springs, CO (US); Rex R. Stevens, Grand Junction, CO (US)

(72) Inventors: Peter J. Tijm, Glenwood Springs, CO (US); Rex R. Stevens, Grand Junction, CO (US)

(73) Assignee: STANDARD ALCOHOL COMPANY OF AMERICA, INC., Denver, CO (US)

(*) Notice: Subject to any disclaimer, the term of this patent is extended or adjusted under 35 U.S.C. 154(b) by 0 days.

(21) Appl. No.: 14/307,173

(22) Filed: Jun. 17, 2014

(65) Prior Publication Data

US 2014/0378560 A1    Dec. 25, 2014

Related U.S. Application Data

(60) Provisional application No. 61/837,413, filed on Jun. 20, 2013.

(51) Int. Cl.
| | |
|---|---|
| *C07C 29/156* | (2006.01) |
| *C07C 29/157* | (2006.01) |
| *B01J 27/051* | (2006.01) |
| *B01J 37/03* | (2006.01) |

(52) U.S. Cl.
CPC ........... *C07C 29/157* (2013.01); *B01J 27/0515* (2013.01); *B01J 37/031* (2013.01); *C07C 29/156* (2013.01); *C07C 2523/22* (2013.01); *C07C 2523/75* (2013.01)

(58) Field of Classification Search
CPC .... C07C 29/157; C07C 29/156; B01J 37/031; B01J 27/0515
See application file for complete search history.

(56) References Cited

U.S. PATENT DOCUMENTS

| | | | |
|---|---|---|---|
| 2,946,738 A | 7/1960 | Gardner et al. | |
| 3,720,602 A | 3/1973 | Riley et al. | |
| 4,122,110 A * | 10/1978 | Sugier et al. ......... | 518/713 |
| 4,177,202 A | 12/1979 | Chang et al. | |
| 4,444,908 A | 4/1984 | Hass | |
| 4,513,100 A | 4/1985 | Fattore et al. | |
| 4,628,113 A | 12/1986 | Current | |
| 4,752,622 A | 6/1988 | Stevens | |
| 4,752,623 A | 6/1988 | Stevens et al. | |
| 4,825,013 A | 4/1989 | Quarderer et al. | |
| 4,831,060 A | 5/1989 | Stevens et al. | |
| 4,840,931 A | 6/1989 | Miller | |
| 4,882,360 A | 11/1989 | Stevens | |
| 5,663,455 A | 9/1997 | Harris et al. | |
| 6,235,677 B1 | 5/2001 | Manzer | |
| 6,319,872 B1 * | 11/2001 | Manzer et al. ......... | 502/66 |
| 7,229,548 B2 | 6/2007 | Riley et al. | |
| 2005/0090688 A1 | 4/2005 | Hagiya | |
| 2010/0210741 A1 | 8/2010 | Kharas | |
| 2010/0331581 A1 | 12/2010 | Kharas | |
| 2011/0319505 A1 | 12/2011 | Janbroers et al. | |
| 2013/0029841 A1 | 1/2013 | Ferrari et al. | |

FOREIGN PATENT DOCUMENTS

| | | |
|---|---|---|
| EP | 0388070 | 9/1990 |
| WO | 8503073 | 7/1985 |
| WO | 0010698 | 3/2000 |
| WO | WO2009009389 | 1/2009 |
| WO | WO2012134490 | 10/2012 |

OTHER PUBLICATIONS

Application No. PCT/US2014/042904, filed Jun. 18, 2014, Applicant: Standard Alcohol Company of America, Inc., International Search Report and Written Opinion dated Oct. 7, 2014, 8 pages.

* cited by examiner

*Primary Examiner* — Sudhakar Katakam
(74) *Attorney, Agent, or Firm* — Geoffrey A. Mantooth; Brian K. Yost

(57) ABSTRACT

Higher mixed alcohols are produced from syngas contacting a catalyst in a reactor. The catalyst has a first component of molybdenum or tungsten, a second component of vanadium, a third component of iron, cobalt, nickel or palladium and optionally a fourth component of a promoter. The first component forms alcohols, while the vanadium and the third component stimulates carbon chain growth to produce higher alcohols.

18 Claims, No Drawings

PRODUCTION OF MIXED ALCOHOLS FROM SYNTHESIS GAS

This application claims the benefit of provisional application Ser. No. 61/837,413, filed Jun. 20, 2013.

FIELD OF THE INVENTION

The present invention relates to a process and catalyst for producing mixed alcohols from synthesis gas.

BACKGROUND OF THE INVENTION

Synthesis gas, or syngas, is made up of hydrogen ($H_2$) and carbon monoxide (CO) and may contain some carbon dioxide ($CO_2$) (and may contain other components as well). Syngas is available from a variety of sources, such as reforming natural gas, coal-bed gas or naphtha, from the gasification of coal, biomass, carbon rich materials, municipal wastes, etc. Using the well-known Fischer-Tropsch process, the syngas is passed over a catalyst and converted to hydrocarbons. When used to produce mixed alcohols, the process is a modified Fischer-Tropsch process and is generally referred to as Mixed Alcohol Synthesis (MAS). Stevens, U.S. Pat. Nos. 4,752,622, 4,752,623 and 4,831,060 disclose MAS catalysts and processes.

Mixed alcohols range from methanol ($C_1$—OH), ethanol ($C_2$—OH), propanol ($C_3$—OH) on up. Alcohols of $C_3$, $C_4$, etc. are referred to as higher alcohols. In general, higher alcohols are preferred for their higher BTU content over the lower alcohols of $C_1$ and $C_2$. In addition to the higher BTU content, higher alcohols have a lower volatility due to their longer molecules.

On its face, the Stevens '622 patent seems promising in disclosing yields of higher alcohols. However, in practice, these results have not been replicated despite numerous attempts. It is desired to produce greater yields of the higher alcohols from the Fischer-Tropsch process in a repeatable manner. There are however reproducible data from Stevens '622 patent catalyst formula producing alcohols comprising 28-53 percent by weight methanol, 39-47% weight ethanol, 6-14% weight propanol, 0.7-3% weight butanol, and 0-2% weight pentanol.

We have found that using vanadium in the catalyst increases the yield of higher alcohols in a repeatable manner. In the prior art, it is known to use the Fischer-Tropsch process to make hydrocarbons, Miller, U.S. Pat. No. 4,840,931. The catalyst has a transition metal taken from the group of cobalt, molybdenum and vanadium. The metals are oxides.

In Quarderer, U.S. Pat. No. 4,825,013, the Fischer-Tropsch process is used to synthesize mixed alcohols, not hydrocarbons. The catalyst is on a support. While the support may contain vanadium, the catalyst does not.

SUMMARY OF THE INVENTION

A process produces a mixture of alcohols from syngas and comprises establishing a catalyst, which catalyst comprises crystalline molybdenum sulfide, crystalline cobalt sulfide and vanadium sulfide in a reactor. The reactor is pressurized and the syngas is passed over the catalyst. The catalyst and the syngas are heated and mixed alcohols are produced.

In one aspect, the establishing the catalyst in a reactor comprises establishing crystalline molybdenum sulfide such that the concentration in the catalyst of molybdenum is 33-43%, by weight, and the concentration of vanadium is 2-14%, by weight, among the molybdenum sulfide, the cobalt sulfide and the vanadium sulfide.

In another aspect, the establishing the catalyst in a reactor comprises establishing crystalline molybdenum sulfide such that the concentration in the catalyst of molybdenum is 36-43%, by weight, and the concentration of vanadium is 10-14%, by weight, among the molybdenum sulfide, the cobalt sulfide and the vanadium sulfide.

In another aspect, potassium is established in the rector in the catalyst.

The step of establishing the catalyst in a reactor comprises establishing crystalline molybdenum sulfide and crystalline vanadium sulfide in a single reaction zone in the reactor.

In another aspect, the alcohol distribution comprises 17-31% by weight methanol, 39-49% weight ethanol, 19-29% weight propanol, 4-12% weight butanol, 0.1-5% weight pentanol, the balance being 0-10% weight hexanol, heptanol, octanol, nananol, decanol, ethers, esters and hydrocarbons.

In another aspect, the crystalline cobalt sulfide comprises metallic cobalt.

In another aspect, the crystalline cobalt sulfide comprises zero valent cobalt.

In another aspect, the crystalline vanadium sulfide comprises metallic vanadium.

In another aspect, the crystalline vanadium sulfide comprises zero valent vanadium.

In another aspect, there further comprises the step of establishing a promoter in the reactor, wherein the promoter comprises potassium carbonate, zirconium and/or zirconium oxide.

A process for producing a mixture of alcohols from syngas comprises establishing a catalyst comprising crystalline molybdenum sulfide, crystalline cobalt sulfide and vanadium in a reactor. The catalyst has the following amounts by weight: molybdenum 33-43%, vanadium 2-14%, cobalt 14-16%, among the molybdenum sulfide, cobalt sulfide and vanadium. The reactor is pressurized and syngas is passed over the catalyst. The catalyst and the syngas are heated and mixed alcohols are produced.

In one aspect, the establishing the catalyst in a reactor comprises establishing crystalline molybdenum sulfide such that the concentration in the catalyst of molybdenum is 36-43%, by weight, and the concentration of vanadium is 10-14%, by weight, among the molybdenum sulfide, the cobalt sulfide and the vanadium.

A modified Fischer-Tropsch mixed alcohols catalyst comprises a first component with at least one element selected from the group consisting of molybdenum or tungsten in free or combined form, a second component comprising vanadium sulfide, a third component with at least one element selected from the group consisting of iron, cobalt and nickel in free or combined form, and a fourth promoter component comprising an alkali or alkaline earth element in free or combined form.

In accordance with one aspect, the catalyst first component comprises crystalline molybdenum sulfide with a concentration in the catalyst of molybdenum is 33-43%, by weight, and the concentration of vanadium is 2-14%, by weight, among the molybdenum sulfide, the cobalt sulfide and the vanadium.

In still another aspect, the fourth promoter component comprises zirconium and/or zirconium oxide.

A modified Fischer-Tropsch mixed alcohols catalyst comprises a first component with at least one element, selected from the group consisting of molybdenum or tungsten in free or combined form, a second component comprising vanadium, a third component with at least one element selected from the group consisting of iron, cobalt and nickel in free or combined form, and a fourth promoter component comprising an alkali or alkaline earth element in free or combined form. The first component is 33-43%, by weight, and the second component is 2-14%, by weight, among the first, second and third components.

DESCRIPTION OF THE PREFERRED EMBODIMENTS

The method described herein passes syngas over a catalyst in the modified Fischer-Tropsch process for producing mixed alcohols. The catalyst is made up of various components, including vanadium. The catalyst increases the yields of higher alcohols, while producing little or no hydrocarbons (such as gasoline or paraffins).

The Fischer-Tropsch process and a catalyst for making mixed alcohols are discussed in detail in Stevens, U.S. Pat. Nos. 4,752,622, 4,752,623 and 4,831,060. The Stevens patents disclose that the catalyst does not contain vanadium and even that vanadium does not significantly alter the character of quantity of the alcohol fraction. It has now surprisingly been found that, contrary to Stevens' disclosure, vanadium in the catalyst composition does unexpectedly and materially contribute to the character and quantity of the alcohol fraction.

The catalyst includes the following:
- a first component having at least one element selected from the group consisting of molybdenum and tungsten in free or combined form;
- a second component of vanadium in free or combined form;
- a third component having at least one element selected from the group consisting of cobalt, iron and nickel in free or combined form;
- a fourth component being a promoter comprising an alkali or alkaline earth element in free or combined form.

As an option, a support can be used.

We believe that the first component forms alcohols, and the third component grows the carbon chains to longer or higher alcohols. We also believe that the second component, particularly when replacing or substituting for the first also stimulates or grows the carbon chains to longer or higher alcohols.

Describing now the components of the catalyst, the first component of the catalyst preferably consists essentially of at least one element selected from the group consisting of molybdenum and tungsten in free or combined form. Molybdenum is preferred.

The first component of the catalyst may be present in the catalyst in "free or combined form" which means that it may be present as a metal, an alloy or a compound of the element. Representative compounds include the sulfides, carbides, oxides, halides, nitrides, borides, salicylides, oxyhalides, carboxylates such as acetates, acetyl acetonates, oxalates, etc., carbonyls, and the like. Representative compounds also include the elements in anionic form such as molybdates, phosphomolybdates, tungstates, phosphotungstates, and the like, and include the alkali, alkaline earth, rare earth and actinide series salts of these anions. The sulfides, carbonyls, carbides and oxides are preferred with the sulfides being most preferred for production of alcohols.

The molybdenum or tungsten may be present in an amount based on the weight of the total catalyst of at least about two percent, preferably at least about 5 percent with an upper limit of about 70 percent and preferably about 37 percent of the catalyst (without promoter or support).

The second component of the catalyst is vanadium, in metallic or combined form, which for the latter means that it may be present as a compound of the element and in particular as the sulfides.

The vanadium may be present in the amount based on the weight of the unpromoted catalyst (having the first, second and third component, but not the fourth component or a support (fifth component)) of at least about 2.5 percent, with an upper limit of 15 percent and preferably about 10 to 14 percent of the unpromoted catalyst. In general, the vanadium substitutes for some of the first component. That is to say, as the amount of vanadium increases, the amount of the first component decreases. The vanadium can be present as crystalline vanadium sulfide, metallic vanadium, zero valent vanadium or metallic, zero valent vanadium.

The third component of the catalyst preferably consists essentially of at least one element selected from the group consisting of iron, cobalt or nickel, or palladium in free or combined form. Cobalt is preferred.

The third component of the catalyst may be present in the catalyst in "free or combined form" which means that it may be present as a metal, an alloy or a compound of the element. Representative compounds include the sulfides, carbides, oxides, halides, nitrides, borides, salicylides oxyhalides, carboxylates such as acetates, acetylacetonates, oxalates, etc., carbonyls, and the like. Representative compounds also include the elements combined with first component elements in anionic form such as iron, cobalt or nickel molybdates, phosphomolybdates, tungstates, phosphotungstates, and the like. The sulfides, carbonyls, carbides and oxides are preferred with the sulfide being most preferred for production of alcohols. The cobalt can be present as crystalline cobalt sulfide with metallic cobalt, zero valent cobalt or metallic, zero valent cobalt.

The cobalt, iron or nickel or mixtures thereof may be present in an amount based on the weight of the total catalyst of at least about two percent, preferably at least about 5 percent with an upper limit of about 70 percent and preferably about 14-16 percent of the unprompted catalyst.

The first and third components may be present in the finished catalyst in an atomic ratio of about 1:10 to about 10:1. Preferably the first and second components are present in a ratio of about 3:1.

The fourth component which is a promoter may consist essentially of one or more alkali elements or alkaline earth elements in free or combined form. Alkali elements include lithium, sodium, potassium, rubidium and cesium. Alkaline earth elements include: beryllium, magnesium, calcium, strontium and barium. Alkali elements and in particular, cesium and potassium, are preferred. Potassium is most preferred. The promoter can comprise potassium carbonate and zirconium oxide.

The promoter may be present in free or combined form as a metal, oxide, hydroxide, carbonate, sulfide or as a salt or a combination of these.

The alkaline, promoter is preferably present at a level sufficient to render the supported catalyst or the bulk catalyst more basic. The promoter is generally present in an amount of at least about 0.05 weight percent as a free element in the finished catalyst. Preferably it is present in an amount of at least about 0.5 percent and most preferably at least 2.0 percent. Large amounts up to about 30 percent of the promoter may be present. Preferably the promoter is present at less than 20 percent.

The promoter may be added as an ingredient to the other components or to the support or may be part of one of the other components such as sodium or potassium molybdate or as an integral part of the support. For example, carbon supports prepared from coconut shells often contain small amounts of alkali metal oxides or hydroxides or the support may contain a substantial amount of the promoter such as when the support is magnesia.

A fifth optional component of the catalyst is a support which may assume any physical form such as pellets, granules, beads, extrudates, etc. The supports may be coprecipitated with the active metal species, or the support in powder form may be treated with the active metal species and then used as is or formed into the aforementioned shapes, or the support may be formed into the aforementioned shapes and then treated with the active catalytic species.

The first three components may be dispersed on the support by methods known in the art. Examples include: impregnation from solution followed by conversion to the active species, vapor deposition intimate physical mixing, sulfiding of either first and/or second component species, precipitation of sulfides in the presence of the support and the like. One or more of these methods may be used.

One alternative method of placing the first four components on the support is known as the incipient wetness technique. Water- or solvent-soluble salts of the metals to be dispersed on the support are chosen. The soluble salts which may be a single salt or more than one salt are dissolved in a quantity of solvent which may be aqueous, nonaqueous or a mixed solvent. A sufficient quantity of the resulting solution is added to the support in an amount no more than will be completely absorbed by the support. The solvent is then evaporated to leave the salt dispersed on the support. Depending on the solubility of the salt chosen and on the quantity of the element desired to be dispersed on the support, this process may be performed once or several times. Impregnations with two or more species may be performed by codissolving them in the solvent or by adding them separately in different quantities or types of solvent. If the species loaded on the support is not the desired one, the loaded support may be treated to convert it to the desired species. For example, oxides may be reduced, with reducing agents such as hydrogen; salts may be decomposed for example by heating, for example, the decomposition of $(NH_4)_2MoS_4$ or $MoS_3$ to $MoS_2$; or one species may be converted to another by contact with a chemical agent, for example sulfiding. A catalyst may be sulfided by contact with a sulfur-containing agent such as $H_2S$.

Preferred methods of placing the first or second components on a support include, for example, impregnation with $(NH_4)_2MoS_4$ followed by decomposition with heat; precipitation of sulfides of the first and/or second components in contact with the support. Placing of the sulfided first and second components on a support is preferably followed by treatment with $H_2$ at elevated temperatures, usually with 20-200 ppm $H_2S$ present.

Exemplary support materials include: the aluminas, basic oxides, the silicas, carbons, or suitable solid compounds of magnesium, calcium, strontium, barium, scandium, yttrium, lanthanum and the rare earths, titanium, zirconium, hafnium, vanadium, niobium, tantalum, thorium, uranium, and zinc. Oxides are exemplary compounds. Preferably the supports are neutral or basic or may be rendered neutral or basic by addition of the alkaline promoters. The aluminas include the alpha, gamma, and eta types. The silicas include for example, silica gel, diatomaceous earth, and crystalline silicates.

The carbon supports, which are preferred supports, include activated carbons such as those prepared from coals and coal-like materials, petroleum-derived carbons and animal- and vegetable-derived carbons. Preferably the carbon support will have a surface area of 1-1500 $m^2/g$, more preferably 10-1000 $m^2/g$ and most preferably 100-500 $m^2/g$ as measured by the BET nitrogen test. Preferably, micropores (<20 Å (<2 nm)) are minimized and at least twenty percent of the volume of the pores comprises pores having a diameter of from about 20 Å to about 600 Å (2-60 nm). Examples include coconut shell charcoal, coals, petroleum cokes, carbons formed by pyrolyzing materials such as vinylidene chloride polymer beads, coal, petroleum coke, lignite, hones, wood, lignin, nut shells, petroleum residues charcoals, etc.

Based upon the weight of the total catalyst, the support, when present, generally comprises at least about 10 percent of the catalyst and generally not more than about 96 percent of the catalyst.

For several reasons the preferred form of the catalyst is the agglomerated sulfide. Certain forms of cobalt/vanadium/molybdenum sulfide are more preferred. Most preferred is agglomerated, cobalt/vanadium/molybdenum sulfide in which the cobalt, vanadium and molybdenum sulfides are coprecipitated.

Methods for making sulfide catalysts are disclosed generally at pages 23-34 of *Sulfide Catalysts Their Properties and Applications*, O. Weisser and S. Landa, Pergamon Press, New York, 1973, the whole which is incorporated herein by reference.

Sulfide catalysts may be made by precipitating iron, cobalt or nickel sulfide in the presence of ammonium heptamolybdate or other thiomolybdates, or thiotungstates and thereafter thermally treating the mixture to convert the thiomolybdate or thiotungstate salt to the sulfide; or as disclosed in U.S. Pat. No. 4,243,553 and U.S. Pat. No. 4,243,554 which are hereby incorporated by reference; or from purchased active combined first and second component sulfides.

Cobalt and molybdenum may be impregnated as salts on a support, then calcined to the oxide and then sulfided with $H_2S$ as taught in GB patent publication No. 2,065,491 which is incorporated herein by reference. A cobalt/molybdenum sulfide may also be precipitated directly on to a support, but the unsupported cobalt/molybdenum sulfide is preferred. Other combinations of first and second component sulfides may be similarly made.

An unsupported catalyst preferably has a surface area of at least 10 $m^2/g$ and more preferably more than 20 $m^2/g$, as measured by the BET nitrogen surface area test.

A preferred method of making a cobalt/vanadium/molybdenum sulfide or other first through third component sulfide is by adding solutions of ammonium heptamolybdate or other equivalent salt, ammonium metavanadate and a cobalt or nickel salt such as the acetate more or less simultaneously to 30 percent acetic acid. This results in the coprecipitation of cobalt/vanadium/molybdenum sulfide. By varying the ratios of cobalt, vanadium and molybdenum or other salts in the solutions one may vary the ratio of cobalt and molybdenum or other elements in the sulfide catalyst. The cobalt/vanadium/molybdenum sulfide or other sulfide may then be separated from the solvent, dried and blended with a fourth component promoter such as $K_2CO_3$ and agglomerating agents and/or pelleting lubricants, then pelleted or extruded and used as the catalyst in the process.

The alkali or alkaline earth promoter may be added to the active catalytic elements prior to, during or after the formation of the sulfide by physical mixing or solution impregnation. The active metal sulfide may then be combined with binders such as bentonite clay, and/or pelleting lubricants such as Sterotex® and formed into shapes for use as a catalyst.

The finished catalyst may be used in a fixed bed, moving bed, fluid bed, slurry bed, ebullated bed or a graded bed wherein concentration and/or activity of the catalyst varies from inlet to outlet in similar manner to known catalysts. The catalyst may be used in powdered form or may be formed into shapes with or without a binder.

Syngas is fed to a reactor, which reactor has the catalyst. Syngas ratios for the feedstock are 0.1 to 10 of hydrogen to carbon monoxide. As an alternative, the hydrogen to carbon monoxide ratio is 0.5 to 5.0. As still another alternative, the hydroen to carbon monoxide ratio is 0.75 to 2.5. It is believed that a feedstock ratio of 1:1 of hydrogen to carbon monoxide is preferred, as too much hydrogen is a chain terminator. Thus, the higher the hydrogen partial pressure and number of hydrogen molecules on the surface of the catalyst, the faster the growing molecules will terminate and become the synthesis product. Feedstock flows are 1,000 to 50,000 liters of syngas per hour per kilogram of crystalline molybdenum sulfide, crystalline cobalt sulfide and crystalline vanadium sulfide. As an alternative, feedstock flow is 1,000 to 25,000 liters per hour per kilogram. As still another alternative, feedstock flow is 2,000 to 15,000 liters per hour per kilogram.

The reactor is operated at pressures ranging from 100 to 10,000 psig. As an alternative, the pressure is 250-5,000 psig. As still another alternative, the pressure is 500-3,000 psig. The reactor is operated at temperatures ranging from 200-375 degrees Celsius. As an alternative, temperatures are 250-380 degrees Celsius and as still another alternative, 275-360 degrees Celsius.

The reactor and its catalyst form a single reaction zone. The syngas is passed through the reactor and in contact with the catalyst. Products exit the reactor. The reactor products need only pass through the reaction zone once and need only pass through one reaction zone. The efficiency of the catalyst is such that only one pass and one reaction zone is needed. Using a single reaction zone saves startup costs, as less reactor hardware is required. Using a single pass saves operational costs, as the throughput through the reactor is much higher with a single pass.

The mixed alcohols may include hexanol, heptanol, octanol, nananol and decanol. The reactor products exit the reactor and undergo separation. In addition to mixed alcohols, the reactor products include oxygenates, such as esters, ethers, ketones and hydrocarbons. These oxygenates need not be separated from the alcohols. Some syngas may pass through the reactor unconverted. The unused syngas can be separated and reused.

EXAMPLE 1

65 g of $(NH_4)_6Mo_7O_{24}4H_2O$ (ammonium heptamolybdate) and 10 g of $NH_4VO_3$ (ammonium metavanadate) was added to 530 mL of $(NH_4)_2S$ (ammonium sulfide). The mixture was stirred and heated at 60-70 degrees C. for one hour. 50 minutes into the one hour, 470 mL of deionized water was added to the solution.

52.5 g of $Co(C_2H_3O_2)_2$ (cobalt acetate) was added to 600 mL of deionized water. This mixture was heated to 60 to 70 degrees C.

The two mixtures were then added to a baffled reactor that had been prepared by adding 700 mL of deionized water and 300 mL of acetic acid and heated to 60 degrees C. The two mixtures were added to the baffled reactor at equivalent rates. The mixture was held at 60 degrees C. for one hour in the reactor. A black precipitant formed. After allowing the precipitant to settle, excess liquid was removed and replaced with deionized water and the mixture was stirred and then allowed to precipitate again. The precipitate readily oxidizes when exposed to air, therefore care was taken to avoid this. The excess water was removed and replaced with acetone, and the mixture was allowed to precipitate.

The precipitate was then calcined by placing it in a kiln that had been purged with inert gas. The precipitate, or burden, was heated to 500 degrees C. and held for an hour.

Once calcine, the catalyst product was mixed with hinder agents. Continuing with the example above, 86.5 g of catalyst were mixed with 26 g of bentonite and about 13 g of potassium carbonate. The mixture was put into a pebble mill for an hour to blend the contents. About 5 g of a pelleting lubricant such as Sterotex was added and the pebble mill was operated for five minutes. The catalyst was separated from the grinding media of the mill by screening. The catalyst was then ready for use.

In use, the catalyst was placed in a reactor. Syngas, having an $H_2$ to CO ratio of 1:1 was fed into the reactor at a temperature of 330-340 degrees C. and pressures of 1500-1540 psi. Conversions of both CO and $H_2$ were 38 to 42 percent. The measured mixed alcohols produced (% weight) are in TABLE 1:

TABLE 1

| Example | 1 | 2 | 3 | 4 | 5 |
|---|---|---|---|---|---|
| $C_1$ | 25-27% | 27-31% | 20% | 24% | 17% |
| $C_2$ | 46-49% | 39-44% | 45% | 48% | 39% |
| $C_3$ | 19-22% | 22-25% | 25% | 20% | 29% |
| $C_4$ | 4-6% | 5-6% | 7% | 5% | 11% |
| $C_5$ | .39-.66% | .51-1.57% | 1.7% | 2.2% | 3.2% |
| $C_6$ | .02-1.9% | .03-.06% | 0% | 1% | .31% |

In addition to the $C_1$-$C_6$ alcohols, amounts of $C_7$-$C_{10}$ alcohols are also obtained.

EXAMPLE 2

The catalyst was prepared with the same components in the same manner as in EXAMPLE 1, except that 5 g of $NH_4VO_3$ was use with a 5 g decrease in the molybdenum component.

The catalyst was placed in a reactor under the same operation conditions as in EXAMPLE 1. Conversion above CO and $H_2$ were 35 to 44%. The mixed alcohol results are given in TABLE 1.

EXAMPLE 3

The catalyst was prepared with the same components in the same manner as in EXAMPLE 1, except that 20 g of $NH_4VO_3$ was used, with a 20 g decrease in the molybdenum component.

The catalyst was placed in a reactor under the same operation conditions as in EXAMPLE 1 Conversion above CO and $H_2$ were 35-44%. The mixed alcohol results are given in TABLE 1.

EXAMPLE 4

The catalyst was prepared with the same components in the same manner as in EXAMPLE 1, except that 25 of $NH_4VO_3$ was used, with a 25 g decrease in the molybdenum component.

The catalyst was placed in a reactor under the same operation conditions as in EXAMPLE 1. Conversion above CO and $H_2$ were 35-44%. These are also given in TABLE 1.

EXAMPLE 5

The catalyst was prepared with the same components in the same manner as in EXAMPLE 4, with 20 g of $NH_4VO_3$%.

The catalyst was placed in a reactor under the same operating conditions as in EXAMPLES 1 and 4, except with a temperature increase to 340 degrees C. Conversion above CO and $H_2$ were 50-52%. These are also given in TABLE 1. The yields of higher alcohols were better than in EXAMPLE 4.

The component amounts (by weight) in the unpromoted catalyst are as follows:

| | |
|---|---|
| EXAMPLE 1 | 36.1% Mo |
| | 4.6% V |
| | 12.9% Co |
| EXAMPLE 2 | 42.3% Mo |
| | 2.5% V |
| | 14.1% Co |
| EXAMPLES 3 and 5 | 36.6% Mo |
| | 10.8% V |
| | 15.5% Co |
| EXAMPLE 4 | 33.9% Mo |
| | 13.8% V |
| | 15.8% Co |

In addition, another example catalyst uses the same components as in EXAMPLE 1, except that 15 g of $NH_4VO_3$ was used with 60 g of the molybdenum compound. The component amounts in the unpromoted catalyst are:

35.7% Mo
7.2 V
13.8 Co

The concentration, by weight, of molybdenum in the catalyst, among the first, second and third components (the unpromoted catalyst), is between 33-43% and preferably between 36-43%. The concentration, by weight, of vanadium in the unpromoted catalyst is 2-14% and preferably 2-11%. The concentration, by weight, of cobalt in the unpromoted catalyst is 14-16% and preferably 15-16%.

The alcohol distribution comprises 17-31% methanol, 39-49% ethanol, 19-29% propanol, 4-12% butanol, 0-5% pentanol, and smaller amounts of $C_7$-$C_{10}$ alcohols, all by weight.

Thus, the yields of the higher alcohols $C_3$—OH to $C_6$—OH were about ¼ of the total. In addition, less methanol was produced than with prior art catalyst, with the remainder, almost ½, being ethanol. As can be seen, the yields of higher alcohols were higher.

The foregoing disclosure is merely illustrative of the principles of this invention and are not to be interpreted in a limiting sense.

The invention claimed is:

1. A process for producing a mixture of alcohols from a syngas comprising the steps of:
    a) establishing a catalyst comprising crystalline molybdenum sulfide, crystalline cobalt sulfide and vanadium sulfide in a reactor;
    b) pressurizing said reactor to 100-10,000 psig;
    c) passing said syngas over said catalyst, the syngas comprising an amount of hydrogen to carbon monoxide of at least 0.5 hydrogen to 5.0 of carbon monoxide;
    d) heating said catalyst and said syngas to 200-375 degrees C.; and
    e) producing said mixed alcohols.

2. A process for producing an alcohol from a syngas as described in claim 1, wherein said step of establishing said catalyst in a reactor comprises the step of establishing crystalline molybdenum sulfide in a reactor such that a concentration of molybdenum in the catalyst is 33-43%, by weight, and the concentration of vanadium is 2-14%, by weight, among the molybdenum sulfide, the cobalt sulfide and the vanadium sulfide.

3. A process for producing an alcohol from a syngas as described in claim 1, wherein said step of establishing said catalyst in a reactor comprises the step of establishing crystalline molybdenum sulfide in a reactor such that a concentration in the catalyst of molybdenum is 36-43%, by weight, and the concentration of vanadium is 2-11%, by weight, among the molybdenum sulfide, the cobalt sulfide and the vanadium sulfide.

4. A process for producing an alcohol from a syngas as described, in claim 1, further comprising the step of establishing potassium in said reactor in the catalyst.

5. A process for producing an alcohol from a syngas as described in claim 1, wherein said step of establishing said catalyst in a reactor comprises the step of establishing crystalline molybdenum sulfide and crystalline vanadium sulfide in a single reaction zone in the reactor.

6. A process for producing an alcohol from a syngas as described in claim 1, wherein said step of producing said alcohol comprises the step of producing predominantly mixed alcohols, some ethers and hydrocarbons, in which the alcohol distribution, is comprised of 17 to 31 weight (wt) % methanol, 39-49 wt % ethanol, 19 to 29 wt % propanol, 4 to 12 wt % butanol, 0.1 to 5 wt % pentanol, the balance being 0 to 10 wt % hexanol, heptanol, octanol, nonanol, decanol, ethers, esters and hydrocarbons.

7. A process for producing an alcohol from a syngas as described in claim 1, wherein said crystalline cobalt sulfide comprises metallic cobalt.

8. A process for producing an alcohol from a syngas as described in claim 1, wherein said crystalline cobalt sulfide comprises zero valent cobalt.

9. A process for producing an alcohol from a syngas as described in claim 1, wherein said crystalline vanadium sulfide comprises metallic vanadium.

10. A process for producing an alcohol from a syngas as described in claim 1, wherein said crystalline vanadium sulfide comprises zero valent vanadium.

11. A process for producing an alcohol from a syngas as described in claim 1, further comprising the step of establishing a promoter in said reactor, wherein said promoter comprises potassium carbonate, zirconium and/or zirconium oxide.

12. A process for producing a mixture of alcohols from a syngas comprising the steps of:
    a) establishing a catalyst comprising crystalline molybdenum sulfide, crystalline cobalt sulfide and vanadium in a reactor, with the following amounts by weight:

| | |
    |---|---|
    | molybdenum | 33-43% |
    | vanadium | 2-14% |
    | cobalt | 14-16% | among the molybdenum sulfide, cobalt sulfide and vanadium;
    b) pressurizing said reactor to 100-10,000 psig;
    c) passing said syngas over said catalyst, the syngas comprising an amount of hydrogen to carbon monoxide of at least 0.5 hydrogen to 5.0 of carbon monoxide;
    d) heating said catalyst and said syngas to 200-375 degrees C.; and
    e) producing said mixed alcohols.

13. A process for producing an alcohol from a syngas as described in claim 12, wherein said step of establishing said catalyst in a reactor comprises the step of establishing crystalline molybdenum sulfide in a reactor such that a concentration in the catalyst of molybdenum is 36-43%, by weight, and the concentration of vanadium is 10-14%, by weight, among the molybdenum sulfide, the cobalt sulfide and the vanadium sulfide.

14. A process for producing a mixture of alcohols from a syngas comprising the steps of;
 a) establishing a catalyst comprising a first component with at least one element selected from the group consisting of molybdenum or tungsten in free or combined form, a second component comprising vanadium sulfide, and a third component with at least one element selected from the group consisting of iron, cobalt and nickel in free or combined form, the catalyst established in a reactor;
 b) pressurizing said reactor to 100-10000 psig;
 c) passing said syngas over said catalyst; the syngas comprising an amount of hydrogen to carbon monoxide of at least 0.5 hydrogen to 5.0 of carbon monoxide;
 d) heating said catalyst and said syngas to 200-375 degrees C.; and
 e) producing said mixed alcohols.

15. A process for producing an alcohol from a syngas as described in claim 3, wherein said step of establishing said catalyst in a reactor further comprises the step of establishing crystalline cobalt sulfide in the reactor such that a concentration of cobalt in the catalyst is 14-16% by weight, among the molybdenum sulfide, the cobalt sulfide and the vanadium sulfide.

16. A process for producing an alcohol from a syngas as described in claim 1, wherein the step of passing said syngas over said catalyst further comprises the step of the syngas comprising a range of hydrogen to carbon monoxide ratios of 0.5:5.0 to 1:1.

17. A process for producing an alcohol from a syngas as described in claim 12, wherein the step of passing said syngas over said catalyst thither comprises the step of the syngas comprising a range of hydrogen to carbon monoxide ratios of 0.5:5.0 to 1:1.

18. A process for producing an alcohol from a syngas as described in claim 14, wherein the step of passing said syngas over said catalyst further comprises the step of the syngas comprising a range of hydrogen to carbon monoxide ratios of 0.5:5.0 to 1:1.

* * * * *